(12) United States Patent
Jeong et al.

(10) Patent No.: US 8,481,300 B2
(45) Date of Patent: Jul. 9, 2013

(54) CONVERSION TO BIOENERGY FROM BIOMASS OF PROTISTAN GRAZERS FEEDING ON AQUATIC PLANT AND/OR ALGAE WHICH CAN SURVIVE AND UPTAKE GREENHOUSE GASES IN THE MIXTURE OF TOXIC GASES AND SUBSTANCE

(75) Inventors: Hae-Jin Jeong, Jeonju-si (KR);
Jae-Yeon Park, Goyang-si (KR);
Yoeng-Do Yoo, Yeosu-si (KR);
Nam-Seon Kang, Gwangju (KR);
Jung-Rhe Rho, Gunsan-si (KR)

(73) Assignee: SNU R&DB Foundation, Seoul (KR)

( * ) Notice: Subject to any disclaimer, the term of this patent is extended or adjusted under 35 U.S.C. 154(b) by 240 days.

(21) Appl. No.: 13/027,629

(22) Filed: Feb. 15, 2011

(65) Prior Publication Data

US 2011/0201064 A1 Aug. 18, 2011

(30) Foreign Application Priority Data

Feb. 16, 2010 (KR) ........................ 10-2010-0013913

(51) Int. Cl.
*C12N 1/12* (2006.01)
*C12N 1/10* (2006.01)
*C12N 1/04* (2006.01)
*C12N 1/02* (2006.01)

(52) U.S. Cl.
USPC .................... 435/257.1; 435/258.1; 435/260; 435/261

(58) Field of Classification Search
None
See application file for complete search history.

(56) References Cited

U.S. PATENT DOCUMENTS

| 5,409,011 A | 4/1995 | Alexeev et al. |
| 5,981,601 A | 11/1999 | Nagley et al. |

FOREIGN PATENT DOCUMENTS

| JP | 11-089555 | 4/1999 |
| JP | 2004-113087 | 4/2004 |
| KR | 20-2009-0010329 | 10/2009 |
| KR | 10-2009-0121659 | 11/2009 |
| WO | 02/064129 | 8/2002 |
| WO | 2007/031443 | 3/2007 |

OTHER PUBLICATIONS

Jeong et al. (Interactions among the toxic dinoflagellate Amphidinium carterae, the heterotrophic dinoflagellate *Oxyrrhis marina*, and the calanoid copepods *Acartia* spp., Mar Ecol Prog Ser 218: 77-86, 2001).*

* cited by examiner

*Primary Examiner* — Suzanne M Noakes
*Assistant Examiner* — Jae W Lee
(74) *Attorney, Agent, or Firm* — Edwards Wildman Palmer LLP

(57) ABSTRACT

Provided are a method for removing and/or absorbing greenhouse gases using aquatic plant and/or algae having a greenhouse gas absorbing performance and resistance to toxic substances, a method for producing bioenergy using predators with high fatty acids, and a method for producing bioenergy including cultivating aquatic plant and/or algae having a greenhouse gas absorbing performance and resistance to toxic substances, while supplying a waste gas mixture to the aquatic plant and/or algae, (S2) cultivating predators having a capability to prey on the aquatic plant and/or algae while supplying the aquatic plant and/or algae to the predators, (S3) harvesting the predators, and (S4) converting the harvested predators into bioenergy.

13 Claims, 5 Drawing Sheets

CONVERSION TO BIOENERGY FROM BIOMASS OF PROTISTAN GRAZERS FEEDING ON AQUATIC PLANT AND/OR ALGAE WHICH CAN SURVIVE AND UPTAKE GREENHOUSE GASES IN THE MIXTURE OF TOXIC GASES AND SUBSTANCE

TECHNICAL FIELD

The present invention relates to a method of removing and/or absorbing greenhouse gases using aquatic plant and/or algae and a method for producing bioenergy from their predators containing high lipids.

BACKGROUND ART

A variety of substances acting as greenhouse gases are well known, and according to the Kyoto protocol adopted on 11 Dec. 1997 in Kyoto, Japan, commitment was made to reduce carbon dioxide, methane, nitrous oxide, perfluorocarbons (PFCs), hydrofluorocarbons (HFCs), and sulfur hexafluoride ($SF_6$).

A process for treating greenhouse gases including carbon dioxide may be largely divided into capturing and fixation. Fixation may include chemical fixation, electrochemical fixation, and biological fixation, etc.

The biological fixation used in the present invention may directly fix carbon dioxide emission sources using suitable aquatic plant such as microalgae, microphytes, seaweeds, see grasses, and the like, resulting in a simple process. Also, the biological fixation may have a variety of industrial applications, for example, the resulting biomasses may be converted to feedstocks or specific chemical substances may be extracted from microorganisms. Currently, leading developed countries are studying practical applications of carbon dioxide fixation by biological methods, however it is very difficult to establish the design and operating conditions of reactors for fixation of carbon dioxide emitted from industry.

Conventionally, technologies for treating carbon dioxide using aquatic plant and/or algae merely comprise supplying, to aquatic plant and/or algae such as microalgae, microphytes, seaweeds, see grasses, and the like, carbon dioxide emitted from power generators, iron works, factories, and the like. It is theoretically possible to remove carbon dioxide using aquatic plant and/or algae, but practically problematic by the following reasons:

Firstly, as a waste gas mixture includes greenhouse gases, and also substances of strong toxicity such as sulfur, carbon oxide, and the like, all aquatic plant and/or algae do not live and grow on greenhouse gases. This is because toxic substances in the waste gas mixture, such as sulfur, carbon oxide, and the like, kill aquatic plant and/or algae. To remove greenhouse gases in the waste gas mixture, aquatic plant and/or algae strong against toxic substances in the waste gas mixture should be used. However, a theory that aquatic plant and/or algae feed on greenhouse gases is currently discovered, but any information about aquatic plant and/or algae strong against toxic substances is not well known. In these circumstances, removal of greenhouse gases using aquatic plant and/or algae is an undeveloped field.

Secondly, deposits of dead microphytes or microalgae may be particularly stuck on a culture container during mass cultivation of aquatic plant and/or algae, so that the quality of cultivated aquatic plant and/or algae may be deteriorated. Also, a transparent culture container may become opaque, which will interrupt the light, and consequently, photosynthesis of aquatic plant and/or algae may be hindered. To solve this problem, a great amount of additional costs may be required.

Thirdly, a variety of bacteria live in a culture container or a pond as well as aquatic plant and/or algae. However, there is no solution to prevent propagation of bacteria, resulting in reduced harvesting efficiency and deteriorated quality of aquatic plant and/or algae.

Fourthly, since it needs to harvest aquatic plant and/or algae having adopted carbon dioxide for removal of carbon dioxide, it requires to harvest aquatic plant and/or algae in a culture container. However, because microphytes and microalgae among aquatic plant and/or algae have a very small size between about 5 and about 40 μm, it is not easy to filter and harvest only microphytes and microalgae in a culture container. Moreover, it is not preferred to keep cultivating aquatic plant and/or algae in a culture container. This is because carbon dioxide may be emitted in a culture solution again when aquatic plant and/or algae having adopted carbon dioxide deteriorate or die, thereby failing to remove carbon dioxide.

Fifthly, a culture solution has a high production cost, and thus, it takes a great amount of costs to cultivate aquatic plant and/or algae.

Recently, with a rapid increase in oil price, interests in new renewable energy increases. In particular, bioenergy, one of new renewable energy, becomes the center of attention as alternative energy of fossil fuels causing global warming. Among bioenergy technologies, bioenergy using aquatic plant and/or algae absorbs greenhouse gases and converts them into energy, and thus, it is considered as effective in reducing carbon dioxide ($CO_2$) and securing energy.

Many energy dependent countries are in urgent need of development of alternative energy. In these circumstances, importance of bioenergy is becoming higher.

DISCLOSURE

Technical Problem

Therefore, it is an object of the invention to provide a method for removing and/or absorbing greenhouse gases using aquatic plant and/or algae having a greenhouse gas absorbing performance and resistance to toxic substances, a method for efficiently using the aquatic plant and/or algae to produce bioenergy, and a method for efficiently producing bioenergy.

Technical Solution

In order to achieve the objects, a method for producing bioenergy according to an aspect of the present invention may include (S1) culturing aquatic plant and/or algae having a greenhouse gas absorbing performance and resistance to toxic substances while supplying greenhouse gases, in general, a waste gas mixture, to the aquatic plant and/or algae, and, (S2) culturing predators having a capability to prey on the aquatic plant and/or algae while supplying the aquatic plant and/or algae to the predators, and, (S3) harvesting the predators, and (S4) converting the harvested predators into bioenergy.

Generally, the waste gas mixture may include greenhouse gases and toxic substances. For example, the greenhouse gases may include, but not limited to, carbon dioxide ($CO_2$), methane ($CH_4$), nitrous oxide ($N_2O$), freons (CFCs), hydrofluorocarbons (HFCs), perfluorocarbons (PFCs), sulfur hexafluoride ($SF_6$), ozone ($O_3$), and mixtures thereof. For example, the toxic substances may include, but not limited to, sulfur and/or carbon oxide. The greenhouse gases may be toxic substances.

The waste gas mixture may be emitted in various places including, but not limited to, power generators, iron works, factories, engines, boilers (district heating, apartment houses), incineration plants, ship, and the like.

The present invention may be characterized by the use of aquatic plant and/or algae having a greenhouse gas absorbing performance and resistance to toxic substances. That is, because the aquatic plant and/or algae of the present invention have resistance to toxic substances, they may not die, but may survive even in the waste gas mixture. Also, with the greenhouse gas absorbing performance, the aquatic plant and/or algae may absorb greenhouse gases in the waste gas mixture through photosynthesis during cultivation, and perform fixation of carbon dioxide by synthesis of organic compounds.

The present invention is not limited to a specific kind of aquatic plant and/or algae if it has a greenhouse gas absorbing performance and resistance to toxic substances. Preferably, the aquatic plant and/or algae may be at least one selected from the group consisting of dinoflagellate including *Amphidinium carterae* and *Prorocentrum minimum*, flagellate including *Heterosigma akashiwo*, *Chattonella* spp., *Rhodomonas salina*, *Isochrysis* spp., and *cryptophytes*, diatom including *Skeletonema costatum*, *Chaetoceros curvisetus*, *Chaetoceros debilis*, *Chaetoceros didymus*, *Chaetoceros socialis*, *Ditylum brightwellii*, *Hemiaulus sinensis*, *Leptocylindrus danicus*, *Odontella aurita*, *Thalassiosira nordenskioeldii*, and *Chaetoceros* spp., macro green algae including sea mustard, kelp, layer, green layer, and agar seaweed, and sea grass. More preferably, the aquatic plant and/or algae may be at least one selected from the group consisting of *Rhodomonas salina*, *Amphidinium carterae*, *Chaetoceros curvisetus*, *Chaetoceros debilis*, *Chaetoceros didymus*, *Chaetoceros socialis*, *Ditylum brightwellii*, *Hemiaulus sinensis*, *Leptocylindrus danicus*, *Odontella aurita*, *Skeletonema costatum*, and *Thalassiosira nordenskioeldii*, most preferably, *Rhodomonas salina*, *Amphidinium carterae*, *Skeletonema costatum*, or mixtures thereof, in terms of a greenhouse gas absorbing performance and resistance to toxic substances.

As shown in Table 1, *Rhodomonas salina* and *Amphidinium carterae* kept living and growing even in the presence of toxic substances in the waste gas mixture, and in particular, *Amphidinium carterae* had a higher absorption rate of greenhouse gases (carbon dioxide) than the other aquatic plant and/or algae (See FIG. 1).

In the step S1, aquatic plant and/or algae having a greenhouse gas absorbing performance and resistance to toxic substances may be cultivated while being supplied with a waste gas mixture, so that the aquatic plant and/or algae may absorb and/or remove greenhouse gases in the waste gas mixture.

The aquatic plant and/or algae may be cultivated in a solution of the waste gas mixture, and a culture tank may include, for example, ash treatment plants, reservoirs such as ponds, limited sea such as bay, estuary and shore, water banks, tanks, air-tight culture containers, and the like. During cultivation, nutrients may be added to help the growth of the aquatic plant and/or algae. Preferably, the solution of the waste gas mixture may be sterile water. The cultivation may follow the cultivation conditions known in the art, and the present invention is not limited to a specific condition if it is suitable to both cultivate aquatic plant and/or algae and synthesize of organic compounds from greenhouse gases in the waste gas mixture and water.

In the step S2, predators having a capability to prey on the aquatic plant and/or algae may be cultivated while being supplying with the aquatic plant and/or algae.

This step may comprise fixing carbon dioxide fixed in the aquatic plant and/or algae during cultivation of the step S1 in predators having preyed on the aquatic plant and/or algae.

The present invention is not limited to specific kind of predators if they have a capability to prey on the aquatic plant and/or algae, and for example, may be hosts, eggs, or larvae of at least one selected from the group consisting of protests, crustacea, helminthes, benthos, and metazoa including *Oxyrrhis marina*, *Gyrodinium* spp., *Gymnodinium* spp., *Polykrikos* spp., *Protoperidinium* spp., *Pfiesteria* spp., *Stoeckeria* spp., *Luciella* spp., tintinnids, naked ciliate, and rotifer. Preferably, the predators may have a high lipid content in consideration of a bioenergy conversion ratio. For example, the predators may be *Oxyrrhis marina*, *Gyrodinium* spp., *Stoeckeria* spp, *Protoperidnium* spp. or mixtures thereof.

Most preferably, the predators may be *Oxyrrhis marina*. *Oxyrrhis marina* has a high lipid content and a high bioenergy conversion ratio, and is advantageous to cultivate aquatic plant and/or algae having fed on greenhouse gases as preys of predators.

Preferably, proper predators may be selected and supplied depending on aquatic plant and/or algae. When aquatic plant and/or algae cultivated in the step S1 are *Amphidinium carterae*, the predators of the step S2 may be preferably *Oxyrrhis marina*.

A method for supplying the aquatic plant and/or algae to the predators may include, for example, harvesting the aquatic plant and/or algae in a culture tank and supplying them to the predators, or inoculating the predators into a culture solution of the aquatic plant and/or algae. Either the former or the latter may be used, however the latter is preferred because it is difficult to harvest aquatic plant and/or algae, provided that aquatic plant and/or algae are small and aquatic plant and/or algae continues to grow as long as growth conditions meet, for example, if only greenhouse gases are provided and aquatic plant and/or algae are not saturated.

The predators according to the present invention may have a capability to prey on bacteria, and thus, may prey on bacteria as well as the aquatic plant and/or algae. Accordingly, the culture tank may be kept clean and a aquatic plant and/or algae culture atmosphere may be improved, and as a result, predators of good quality may be harvested.

In the step S3, the predators having fed on the aquatic plant and/or algae may be harvested.

To harvest the predators, a variety of means well known in the art may be used, for example, including, but not limited to, a centrifugal separator, a porous filter mesh, a glass fiber filter paper, and the like.

The predators are relatively larger in size, and may be easier to harvest than the aquatic plant and/or algae, and this will be a significant advantage of the present invention.

Also, the method for producing bioenergy according to the present invention may further include sterilizing the solution remaining after harvesting the predators in the step S3, and re-providing the sterile solution to the step S1 for cultivating the aquatic plant and/or algae. The solution remaining after harvesting the predators may include nutritive salts. Accordingly, the sterile solution may have a good effect on cultivation of the aquatic plant and/or algae.

In the step S4, the harvested predators may be converted into bioenergy.

The predators according to the present invention may feed on the aquatic plant and/or algae, and accordingly, carbon dioxide fixed in the aquatic plant and/or algae may be fixed in the predators. Such predators may be used as biomasses.

The lipid content in the predators having fed on the aquatic plant and/or algae is relatively higher than that of the aquatic plant and/or algae, and it is easy to harvest the predators because the predators are relatively larger than the aquatic plant and/or algae, and accordingly, it may be more effective and economical to obtain bioenergy from the predators than to directly obtain bioenergy from the aquatic plant and/or algae.

To convert the predators into bioenergy, a variety of methods known in the art may be used, for example, as disclosed in U.S. Pat. Nos. 5,981,601, 5,409,011, Europe Patent Publication No. 01945741, and Europe Patent Publication No. 01368017. For example, a method for extracting biodiesel may include refrigerating and freeze-drying the harvested predators, extracting components in the predators by solvent extraction of the dried predators using methanol, chloroform, and distilled water, separating a chloroform layer containing fatty acids and their derivatives, evaporating only chloroform to separate pure fatty acids and their derivatives, and transesterifying the separated fatty acids and their derivatives using methanolic HCl.

More specifically, the harvested predators may be converted into bioenergy by rapidly refrigerating the predators at temperature between −90 and −70° C., drying the predators using a freeze dryer, dissolving the dried predators in distilled water, mixing the result with a solvent, that is, methanol and chloroform, putting the mixture in a sonicator for about 2 to about 10 hours and extracting components in cells using ultrasonic waves, such that the ultrasonically milled sample has at a ratio of 1:1:0.9=methanol:chloroform:distilled water and is divided into two layers including an upper layer of distilled water and methanol and a lower layer of chloroform, separating the two layers using a separatory funnel, taking the chloroform layer containing fatty acids and their derivatives, evaporating chloroform using an evaporator to obtain pure fatty acids and their derivatives, adding methanol HCl to the extracted fatty acids and their derivatives, and transesterifying them at 80° C. for 2 hours through, and however the present invention is not limited in this regard.

The method for producing bioenergy according to the present invention may further include, before the step S1, selecting aquatic plant and/or algae having a greenhouse gas absorbing performance and resistance to toxic substances, and predators having a capability to prey on the aquatic plant and/or algae.

In the selecting of aquatic plant and/or algae having a greenhouse gas absorbing performance and resistance to toxic substances, aquatic plant and/or algae that may maintain a greenhouse gas absorbing performance even in the present of toxic substances may be preferably selected. Accordingly, it may ensure the greenhouse gas removing effectiveness in spite of toxic substances included in the waste gas mixture.

Also, in the selecting of predators having a capability to prey on the aquatic plant and/or algae, predators having at least one of a high growth rate, a high ratio of transferring carbon dioxide fixed in the aquatic plant and/or algae to the predators, and a high conversion ratio into lipids may be more preferably selected, and most preferably, predators having a high conversion ratio into lipids may be selected.

According to another aspect, the present invention provides a method for removing and/or absorbing greenhouse gases using aquatic plant and/or algae having a greenhouse gas absorbing performance and resistance to toxic substances, the aquatic plant and/or algae being at least one of selected from the group consisting of *Rhodomonas salina, Amphidinium carterae, Chaetoceros curvisetus, Chaetoceros debilis, Chaetoceros didymus, Chaetoceros socialis, Ditylum brightwellii, Hemiaulus sinensis, Leptocylindrus danicus, Odontella aurita, Skeletonema costatum*, and *Thalassiosira nordenskioeldii*.

The inventors discovered that these aquatic plant and/or algae have a greenhouse gas absorbing performance and resistance to toxic substances, and completed the present invention.

With resistance to toxic substances, the aquatic plant and/or algae may survive in waste gas mixture, but may not die. Accordingly, this viability may enable the aquatic plant and/or algae to keep absorbing and/or removing greenhouse gases, thereby supporting the effectiveness for removing greenhouse gases in the waste gas mixture.

The aquatic plant and/or algae having a greenhouse gas absorbing performance and resistance to toxic substances, provided in the present invention, may be at least one of the group consisting of dinoflagellatae including *Amphidinium carterae* and *Prorocentrum minimum*, flagellatae including *Heterosigma akashiwo, Chattonella* spp., *Rhodomonas salina, Isochrysis* spp., and *cryptophytes*, diatom including *Skeletonema costatum, Chaetoceros curvisetus, Chaetoceros debilis, Chaetoceros didymus, Chaetoceros socialis, Ditylum brightwellii, Hemiaulus sinensis, Leptocylindrus danicus, Odontella aurita, Thalassiosira nordenskioeldii*, and *Chaetoceros* spp., macro green algae including sea mustard, kelp, layer, green layer, and agar seaweed, and sea grasses. More preferably, the aquatic plant and/or algae may be at least one selected from the group consisting of *Rhodomonas salina, Amphidinium carterae, Chaetoceros curvisetus, Chaetoceros debilis, Chaetoceros didymus, Chaetoceros socialis, Ditylum brightwellii, Hemiaulus sinensis, Leptocylindrus danicus, Odontella aurita, Skeletonema costatum*, and *Thalassiosira nordenskioeldii*, most preferably, *Rhodomonas salina, Amphidinium carterae, Skeletonema costatum*, or mixtures thereof.

As disclosed in Table 1, *Rhodomonas salina* and *Amphidinium carterae* kept living and growing even in the presence of toxic substances in the waste gas mixture, and in particular, *Amphidinium carterae* had a higher absorption rate of greenhouse gas (carbon dioxide) than the other organisms (See FIG. 1).

Among the aquatic plant and/or algae provided in the present invention, a proper aquatic plant and/or algae may be selected depending on the kinds of greenhouse gases and toxic substances in the waste gas mixture to be absorbed and/or removed. According to the embodiments of the present invention, aquatic plant and/or algae that may survive and live in a waste gas mixture generated during burning of coal, petroleum (gasoline and diesel) and natural gas and may keep removing greenhouse gases in the waste gas mixture, in particular, carbon dioxide, may be *Rhodomonas salina, Amphidinium carterae, Chaetoceros curvisetus, Chaetoceros debilis, Chaetoceros didymus, Chaetoceros socialis, Ditylum brightwellii, Hemiaulus sinensis, Leptocylindrus danicus, Odontella aurita, Skeletonema costatum*, or *Thalassiosira nordenskioeldii*.

According to still another aspect, the present invention provides a method for producing bioenergy using predators with high lipids, for example, *Oxyrrhis marina, Protoperidinium* spp., *Gyrodinium* spp., *Stoeckeria algicida*, or mixtures thereof.

In the present invention, the high fatty acid means more than 10%, or more preferably 15%, and most preferably 20% of fatty acid contents among dried biomass weight.

The inventors discovered that these predators have a high lipid content and a high conversion ratio into bioenergy, preferably, 40 to 70% of the total lipid content, and concluded the predators as effective biomasses, and they completed the present invention.

Preys of the predators may be properly selected as known in the art depending on the kinds of predators. For example, the preys may be food wastes or aquatic plant and/or algae, preferably, aquatic plant and/or algae having absorbed greenhouse gases and fixed carbon dioxide, and more preferably, aquatic plant and/or algae having a greenhouse gas absorbing performance and resistance to toxic substances, cultivated while being supplied with a waste gas mixture.

Such predators have high lipids, stronger viability than aquatic plant and/or algae, and a capability to prey on bacteria, and accordingly, they are advantageous in keeping cultivating. Also, the predators are relatively large, and accordingly, they are favorably easy to harvest.

Effect of the Invention

According to the present invention, aquatic plant and/or algae may live, but may not die, even in the presence of toxic substances in a waste gas mixture and may absorb greenhouse gases, and accordingly, the use of aquatic plant and/or algae may practically enable removal of greenhouse gases in the waste gas mixture and reduction in an emission amount of greenhouse gases to an atmosphere to prevent global warming, and as a result, the costs of emission trading for greenhouse gas emissions may be reduced.

Also, aquatic plant and/or algae may be supplied as preys of predators, thereby preventing further contamination from occurring due to mass cultivation of the aquatic plant and/or algae.

Furthermore, bioenergy may be produced using lipids of predators having fed on aquatic plant and/or algae that had absorbed greenhouse gases and fixed carbon dioxide, thereby reducing the production costs of bioenergy. Also, the predators may be divided two or three times a day while feeding on aquatic plant and/or algae, and consequently, a large amount of biomasses may be harvested in a short time. Accordingly, it may result in sufficient supply of raw materials of bioenergy and reduced production costs of bioenergy.

In addition, because solution remaining after filtering and harvesting predators includes nutritive salts, the solution may be re-cycled and re-used as culture solution of aquatic plant and/or algae, so that the costs required to cultivate the aquatic plant and/or algae may be considerably reduced.

As described above, the present invention may solve the critical problems of bioenergy technology for treating green gas using aquatic plant and/or algae that have been unsolved so far, and may have excellent effects for obtaining a large amount of biomasses and utilizing the biomasses as energy.

DESCRIPTION OF DRAWINGS

These and other features, aspects, and advantages of preferred embodiments of the present invention will be more fully described in the following detailed description, taken accompanying drawings.

MODE FOR INVENTION

Figure 1:
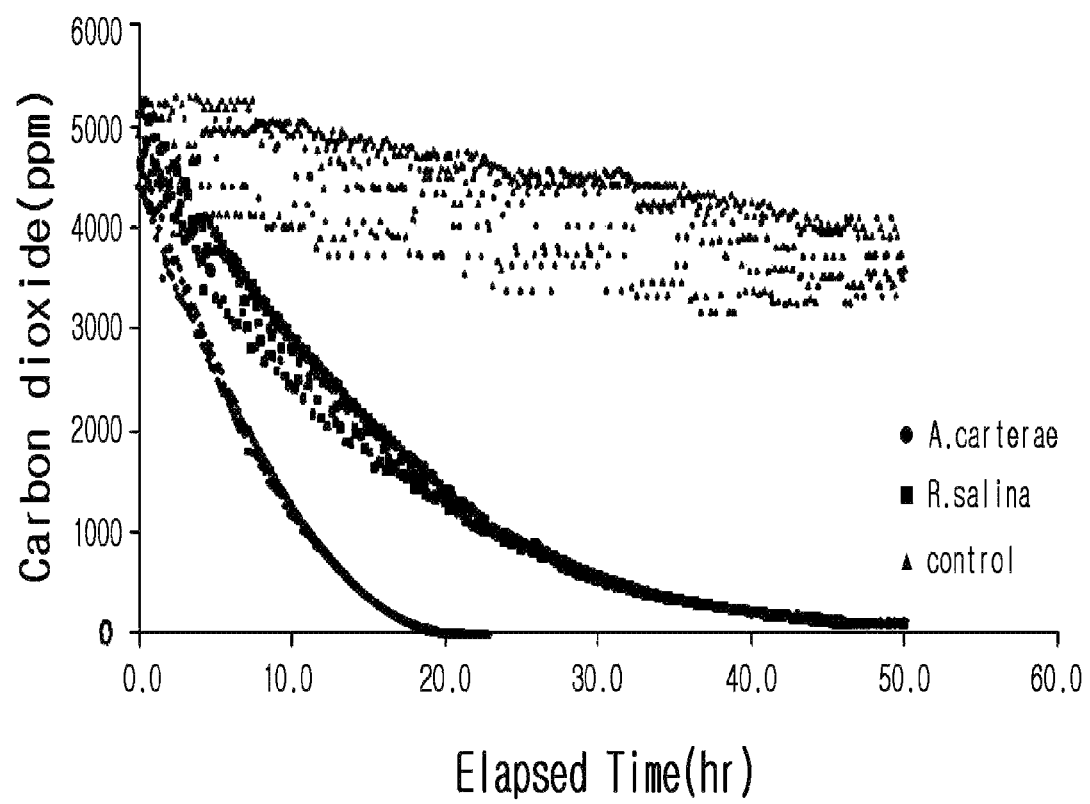
FIG. 1 is a graph illustrating comparison of carbon dioxide absorption rates of between *Amphidinium carterae* (circle) and *Rhodomonas salina* (square).

Hereinafter, the present invention will be described in detail with reference to the accompanying drawings. Prior to the description, it should be understood that the terms used in the specification and appended claims should not be construed as limited to general and dictionary meanings, but interpreted based on the meanings and concepts corresponding to technical aspects of the present invention on the basis of the principle that the inventor is allowed to define terms appropriately for the best explanation. Therefore, the description proposed herein is just a preferable example for the purpose of illustrations only, not intended to limit the scope of the invention, so it should be understood that other equivalents and modifications could be made thereto without departing from the spirit and scope of the invention.

EXAMPLE 1

Absorption of Greenhouse Gases by Aquatic Plant and/or Algae

1) Selection of Optimum Aquatic Plant and/or Algae

To select aquatic plant and/or algae that are resistant to toxic substances in a waste gas mixture, that is, may survive, but may not die, in the presence of toxic substances, and have a high adsorption rate of greenhouse gases such as carbon dioxide and the like, aquatic plant and/or algae were cultivated while being supplied with a culture solution oversaturated with a waste gas mixture (combustion gas) generated during burning of fossil fuels including coal, petroleum (gasoline and diesel), and natural gas (LNG) dissolved therein through aeration. Then, species of aquatic plant and/or algae that may survive in the presence of the culture solution oversaturated with dissolved combustion gas were selected.

Dinoflagellatae including *Amphidinium carterae, Prorocentrum minimum* and *Heterocapsa triquetra*, flagellatae including *Heterosigma akashiwo* and *Rhodomonas salina*, and diatom including *Skeletonema costatum* and *Chaetoceros curvisetus*, were inoculated into the culture solution having combustion gas dissolved therein, and were cultivated under conditions of temperature of 20° C., a light/dark cycle of 14:10, and illuminance of 3000 Lux for 5 days. The features of the cultivated aquatic plant and/or algae were observed, such as survival or death, a growth rate, and cell mutation, and the results are shown in Table 1.

TABLE 1

Survival/death and reaction of aquatic plant and/or algae in a culture solution having combustion gas dissolved therein

| Species | | Cell size (μm) | Survival/ death | Note |
|---|---|---|---|---|
| Flagellatae | *Heterocapsa rotundata* | 5.8 | Δ | Initially, it hardly survives, but starts to slowly grow in 5 days or longer |
| | *Rhodomonas salina* | 6.7 | ○ | It grows 70% when compared with controls |
| | *Amphidinium carterae* | 9.7 | ○ | |

TABLE 1-continued

Survival/death and reaction of aquatic plant and/or algae in a culture solution having combustion gas dissolved therein

| Species | | Cell size (μm) | Survival/ death | Note |
|---|---|---|---|---|
| | Prorocentrum minimum | 12.1 | Δ | Initially, it hardly |
| | Prorocentrum triestinum | 12.6 | Δ | survives, but starts |
| | Prorocentrum donghaiense | 13.3 | Δ | to slowly grow in 5 days or longer |
| | Heterocapsa triquetra | 15.0 | Δ | |
| | Gymnodinium impudicum | 17.8 | Δ | It survives but |
| | Karenia brevis | 20.3 | Δ | hardly grows |
| | Scrippsiella trochoidea | 22.8 | Δ | |
| | Cochlodinium polykrikoides | 25.9 | Δ | |
| | Prorocentrum micans | 26.6 | X | It dies within 24 hours |
| | Alexandrium tamarense | 28.1 | Δ | It survives but hardly grows |
| | Akashiwo sanguinea | 30.8 | X | It dies within 24 |
| | Alexandrium catenella | 32.6 | X | hours |
| | Gymnodinium catenatum | 33.9 | Δ | It survives but hardly grows |
| | Gonyaulax polygramma | 32.5 | X | It dies within 24 |
| | Lingulodinium polyedrum | 38.2 | X | hours |
| Diatom | Asterionellopsis glacialis | 30/150 | Δ | It survives but |
| | Asterionellopsis kariana | 12-30 | Δ | hardly grows |
| | Chaetoceros affine | 14-20 | Δ | Chains shortened, |
| | Chaetoceros compressus | 5-40 | Δ | and cell walls |
| | Chaetoceros curvisetus | 6-40 | ○ | weakened |
| | Chaetoceros debilis | 10-40 | ○ | |
| | Chaetoceros didymus | 10-40 | ○ | |
| | Chaetoceros socialis | 3-15 | ○ | |
| | Cylindrotheca closterium | 30 | Δ | Cell size reduced |
| | Ditylum brightwellii | 90 | ○ | Cell walls weakened |
| | Eucampia zodiacus | 20-50 | Δ | |
| | Guinardia delicatula | 10-30 | Δ | |
| | Hemiaulus sinensis | 45-55 | ○ | |
| | Leptocylindrus danicus | 5-10 | ○ | Chains shortened, |
| | Odontella aurita | 48 | ○ | and cell walls weakened |
| | Rhizosolenia pungens | 5-30 | Δ | It survives but |
| | Rhizosolenia setigera | 5-40 | Δ | hardly grows |
| | Rhizosolenia styliformis | 15-40 | Δ | |
| | Skeletonema costatum | 5 | ○ | Chains shortened, |
| | Thalassiosira delicatula | 5 | Δ | and cell walls |
| | Thalassiosira gravida | 20 | Δ | weakened |
| | Thalassiosira lotula | 25 | Δ | |
| | Thalassiosira nordenskioeldii | 4 | ○ | |

○: high survival ratio,
Δ: low survival ratio,
X: died
*List of microalgae in the experiment to test the influence of exhaust gas Among the aquatic plant and/or algae used in the experiment, flagellatae including *Amphidinium carterae* and the like and diatom including *Skeletonema costatum* and the like, showed a growth rate of 70% when compared with cases where they are cultivated in a general culture solution. After 7 days passed, *Amphidinium carterae* grew at the same growth rate as in a general culture solution. However, *Skeletonema costatum* had much cell mutation or damage during the experiment, and as the mutation or damage was not overcome, *Skeletonema costatum* exhibited a significant growth delay in 7 days or longer. Accordingly, *Amphidinium carterae* was selected as the most suitable aquatic plant and/or algae for absorbing greenhouse gases.

2) Comparison of Carbon Dioxide Absorption Rates Between Species of Aquatic Plant and/or Algae Among flagellatae, *Amphidinium carterae* and *Rhodomonas salina* were compared in carbon dioxide absorption rates when exposed to combustion gas, wherein *Amphidinium carterae* has a growth rate of 70% and *Rhodomonas salina* has a growth rate of 60% under usual conditions. 7 L of each culture solution of *Amphidinium carterae* and *Rhodomonas salina* ($21 \times 10^5$ cells/ml) was putted into a 20 L carboy, and combustion gas emitted from a portable power generator (using gasoline) was supplied such that the carbon dioxide concentration in the carboy was about 4800 ppm. After the carboy was sealed, the time to completely remove carbon dioxide was measured.

The result showed that *Amphidinium carterae* removed carbon dioxide faster at least twice than *Rhodomonas salina* (See FIG. 1).

3) Greenhouse Gas Adsorbing Capability of the Selected Aquatic Plant and/or Algae, *Amphidinium carterae*

Figure 2:
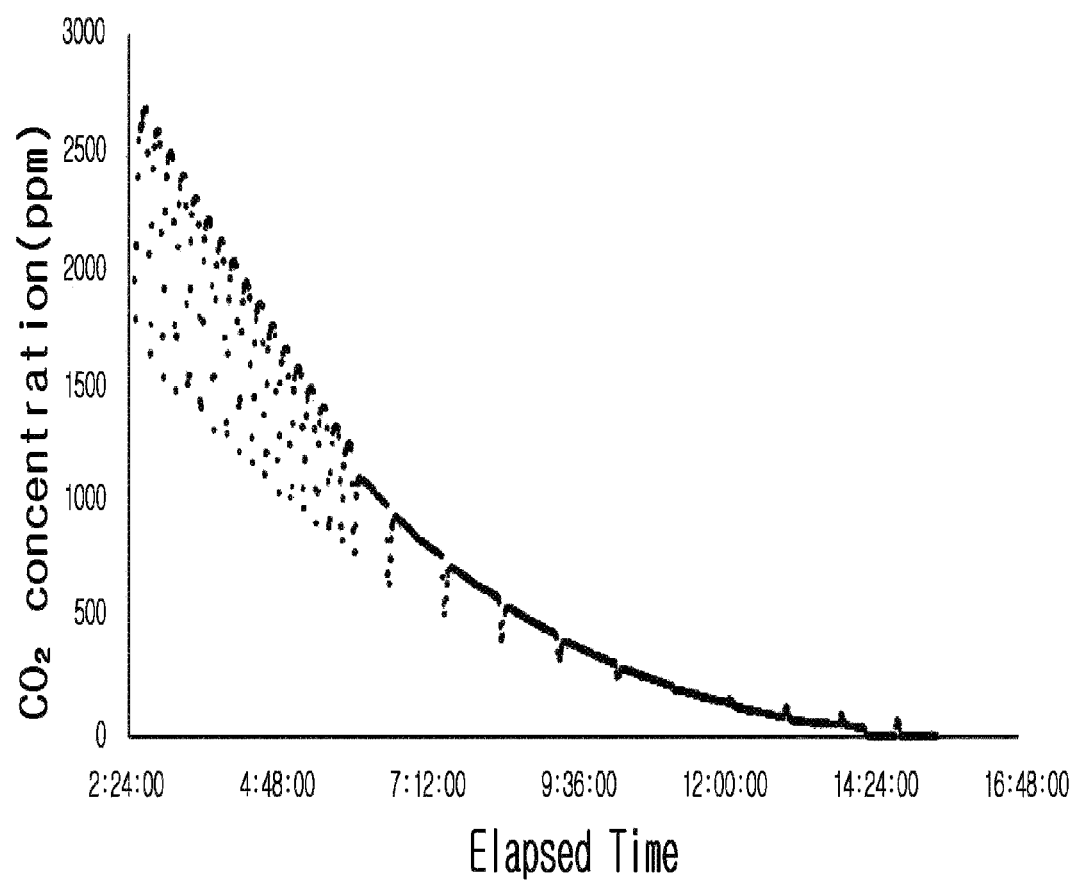
FIG. 2 is a graph illustrating a carbon dioxide absorbing capability of *Amphidinium carterae*.

The selected aquatic plant and/or algae, *Amphidinium carterae* completely absorbed carbon dioxide in 20 hours, while it took 50 hours or longer for *Rhodomonas salina* to completely remove carbon dioxide. Accordingly, it was found that *Amphidinium carterae* was the most suitable aquatic plant and/or algae for reducing carbon dioxide among the aquatic plant and/or algae used in the experiment (See FIG. 2).

An experiment about the relationship between the surface area exposed to combustion gas and a carbon dioxide absorption rate was carried out to determine a culture tank having the highest absorption efficiency of carbon dioxide when designing or selecting a culture tank for reducing carbon dioxide using aquatic plant and/or algae. The 20 L PC carboy used in the experiment was of a vertical type, and the carboy had a cylindrical shape and a diameter of about 25 cm. When the carboy was filled with a culture solution, a contact area of a surface layer of the culture solution with an atmosphere was about 530 $cm^2$. However, when the carboy was horizontally laid, the height of the carboy was about 37 cm, and a contact area of a surface layer of the culture solution with an atmosphere was about 925 $cm^2$. A difference in surface area therebetween was nearly twice. To survey the relationship between the surface area exposed to combustion gas and a carbon dioxide absorption rate using this feature, *Amphidinium carterae* was cultivated up to the concentration of $2 \times 10^5$ cells/ml, 7 L of each culture solution was putted into a 20 L PC carboy, and combustion gas emitted from a portable power generator (using gasoline) was supplied into the carboy such that the carbon dioxide concentration was about 4500 ppm. After the carboys were sealed, one carboy was vertically erected such that the surface area was about 530 $cm^2$ and the other was horizontally laid such that the surface area was about 925 $cm^2$, and a change in concentration of carbon dioxide was observed using TSI 7535 carbon dioxide meter. A carboy receiving a culture solution without *Amphidinium carterae* was used as a control.

Figure 3:
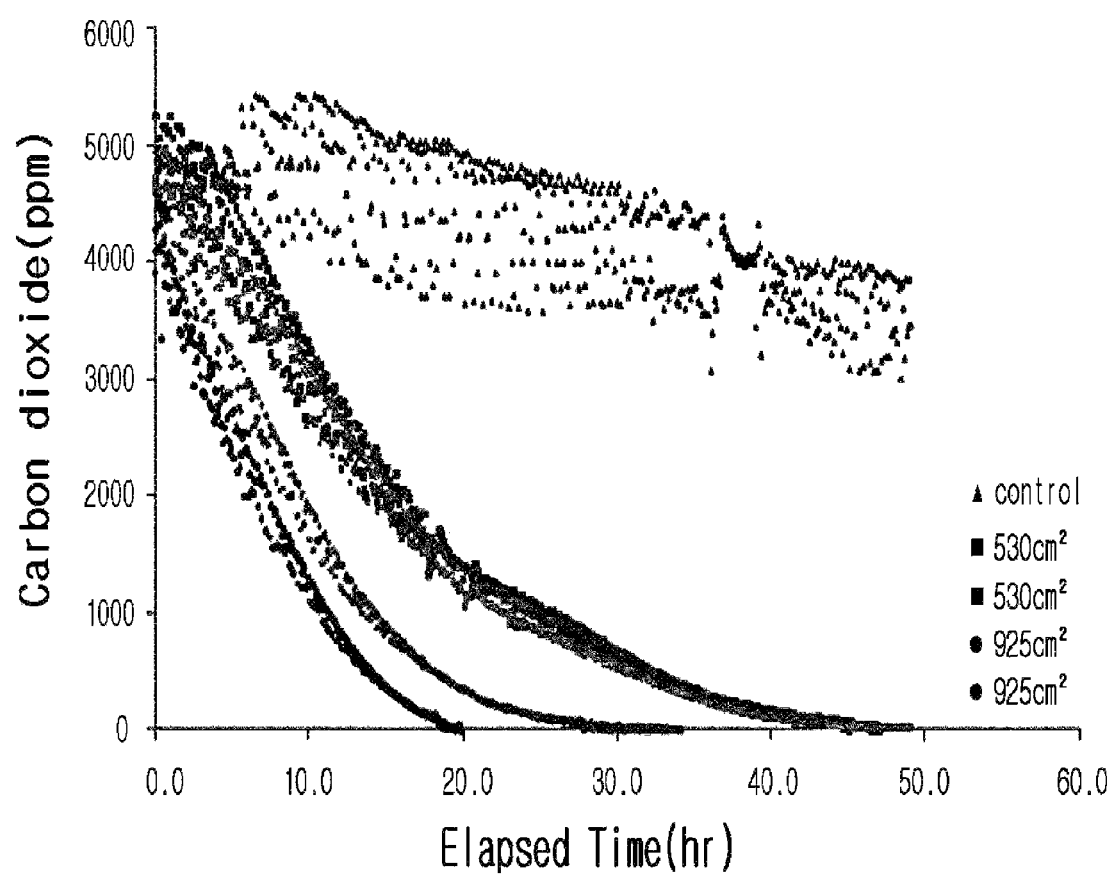
FIG. 3 is a graph illustrating a change in carbon dioxide absorption rate of *Amphidinium carterae* based on the surface area contacted with greenhouse gases.

The experiment results showed that the sample of a horizontal type having a larger surface area removed carbon dioxide faster. Specifically, it took about 24 hours for the horizontally arranged carboy to completely remove carbon dioxide of 4500 ppm, and it took about 45 hours for the vertically arranged carboy to do so (See FIG. 3).

4) Removal Effects of Carbon Dioxide Using Aquatic Plant and/or Algae

It is known that Amphidinium carterae has an average cell size of 9.7 μm, and fixes about 0.005 mmol of carbon dioxide a day on average. Assuming *Amphidinium carterae* cultivated up to a concentration of $2 \times 10^5$ cells/ml is used and the number of cells increases three times for 1 day because *Amphidinium carterae* is divided once to three times per day, an amount of removed carbon dioxide may be calculated as following (when a 5 ton-scale culture tank is used):

$$0.005 \ \mu mol \ C/cell/d \ \times (200{,}000 \ cells/ml) \times$$
$$(10^6 \ ml/t) \times 3 \ (\text{divide 1.5 time, increase three times}) \times 44$$
$$(\text{molecular weight of } CO_2) = 132 \ kg \ CO_2/t/d \ \times 5 \ m^3 =$$
$$0.66 \ ton \ CO_2/5 \ m^3/d \times 356 \ d/yr = 240.9 \ ton \ CO_2/5 \ m^3/yr$$

In other words, assuming *Amphidinium carterae* removes carbon dioxide while being cultivated in a 5 ton-scale tank, carbon dioxide of about 241 tons per year may be removed. Assuming the costs of emission trading are 20 dollars per ton, the costs of about 4800 dollars may be saved.

Assuming a carbon dioxide absorption rate per 1 ha forest is 7.3 ton a year, the saved costs may have effects of making forests of about 100,000 pyeong, that is, about 33 ha. Also, assuming an annual carbon dioxide reduction amount for each vehicle is 3 tons, the saved costs may have effects of replacing 80 gasoline vehicles by electric vehicles representing low-emission environmental friendly vehicles. As the costs required to cultivate 5 tons of *Amphidinium carterae* are much smaller than those of making forests of about 100,000 pyeong or those of replacing gasoline vehicles by electric vehicles, considerable economical effects may be obtained as well as carbon dioxide reduction effects.

EXAMPLE 2

Selection of Predators and Increase in Population of Predators

1) Selection of Predators Suitable for Selected Aquatic Plant and/or Algae

To select predators of the selected aquatic plant and/or algae, *Amphidinium carterae*, field samples were gathered each season in 23 coastal vertex across the country (Incheon, Sihwa, Pyeongtaek, Seosan, Daecheon, Gunsan, Gyeokpo, Mokpo, Goheung, Gwangyang, Yeosu, Jinhae, Masan, Tongyeong, Busan, Ulsan, Pohang, Uljin, Samcheok, Donghae, Jumunjin, Sokcho). The samples were filtered through a Nitex screen of 154 μm mesh. The samples were cultivated, feeding on Amphidinium carterae of 8,000 cells/ml concentration, while being rotated at 0.9 rpm in a rotating wheel. In this instance, culture temperature was 20° C., and illuminance was 1200 Lux. After 2 days passed, each sample was observed with a microscope, and predators grown on *Amphidinium carterae* were isolated. The obtained predators were flagellatea including *Oblea rotunda*, *Oxyrrhis marina*, *Gyrodinium dominans*, *Gyrodinium guttula*, *Pfiesteria piscicida*, *Luciella masanensis*, and *Polykrikos kofoidii*. Among them, *Amphidinium carterae* exhibited a highest ingestion rate, and *Oxyrrhis marina* showed a highest growth rate.

Figure 4:
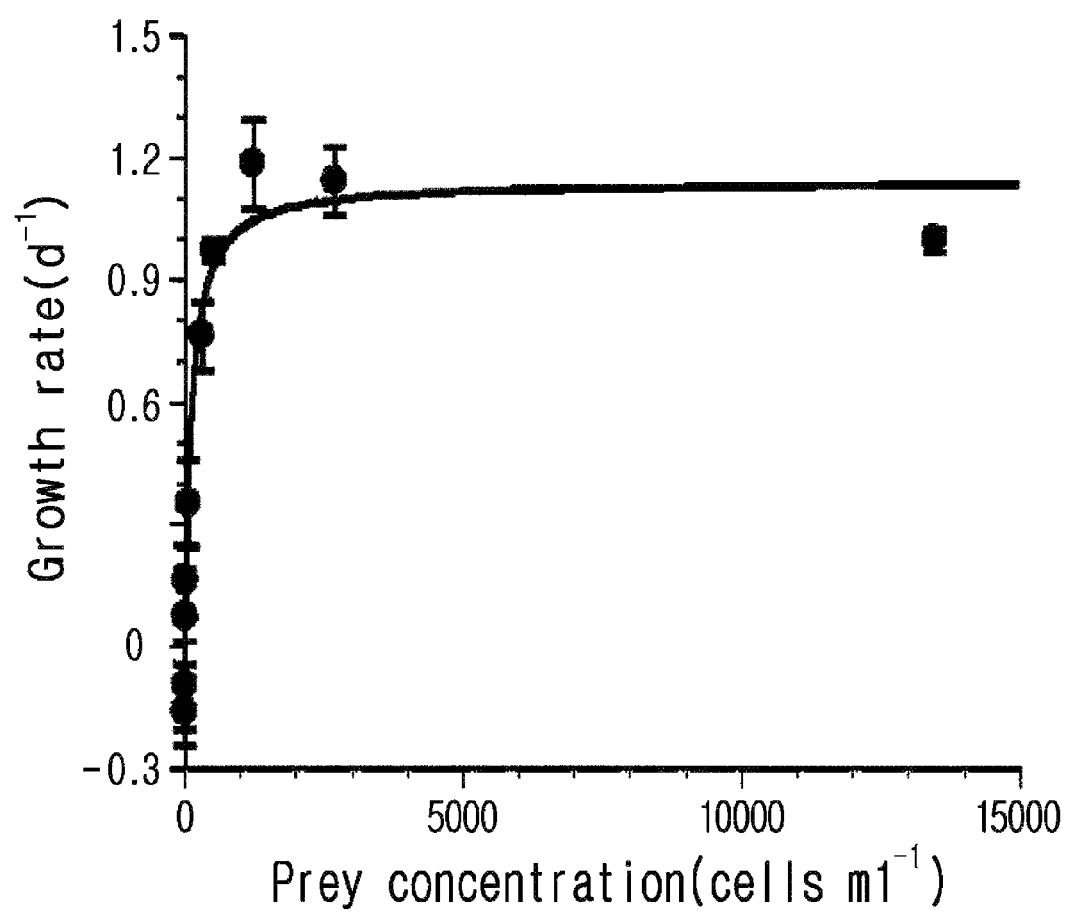
FIG. 4 is a graph illustrating a growth rate of *Oxyrrhis marina* cultivated while feeding on *Amphidinium carterae*.

Also, *Oxyrrhis marina* showed a maximum growth rate when a prey concentration of *Amphidinium carterae* was 1200 cells/ml or more (See FIG. 4). However, the growth rate was maintained in a higher concentration range.

Figure 5:
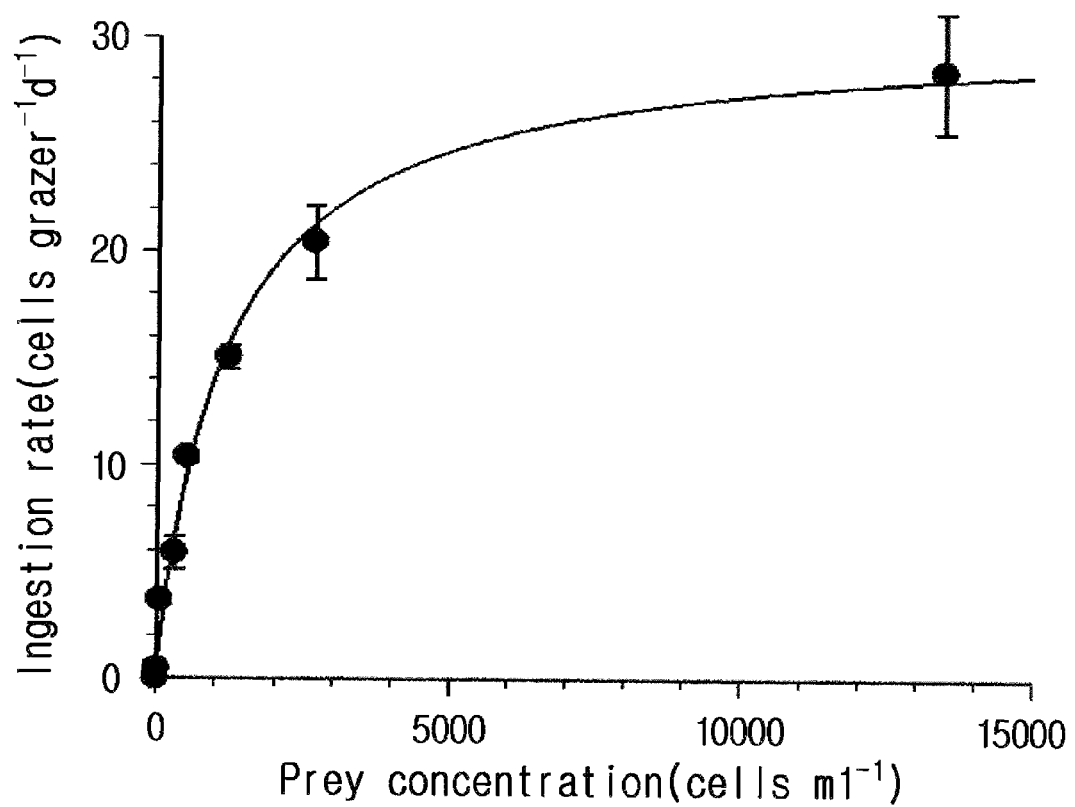
FIG. 5 is a graph illustrating an ingestion rate of *Oxyrrhis marina* having fed on *Amphidinium carterae*.

The ingestion rate of *Oxyrrhis marina* rapidly increased until a cell concentration of *Amphidinium carterae* reaches 2,700 cells/ml, and slowly increased in a higher concentration range (See FIG. 5).

One *Oxyrrhis marina* fed on a maximum of 30 *Amphidinium carterae* a day, and its maximum growth rate was 1.16/d. In other words, assuming *Oxyrrhis marina* is divided 1.7 times a day, one *Oxyrrhis marina* is divided into 32 *Oxyrrhis marina* 5 times for 3 days. Also, *Oxyrrhis marina* feeds on heterotrophic microphytes, bacteria, and granular organic substances as well as aquatic plant and/or algae, resulting in little pollution and easy cultivation.

Accordingly, it is expected that biomasses convertible into a large amount of bioenergy in a short time will be harvested, resulting in sufficient supply of raw materials of bioenergy and reduced production costs of bioenergy.

EXAMPLE 3

Harvest of Predators

To improve the harvesting efficiency of *Oxyrrhis marina* in this experiment, a continuous centrifugal separator was driven at 5000 rpm in the lab. The harvested *Oxyrrhis marina* was light pink. The harvested biomasses were freeze-dried and used in an experiment for bioenergy production.

Although this embodiment shows a centrifugal separator was used in consideration of harvesting efficiency and basic experimental materials, a porous filter net or a glass fiber filter paper of a low cost may be used in an actual system.

1 ton of *Oxyrrhis marina* was putted into a 3 ton-scale tank at a concentration of 600 cells/ml, and cultivated for 3 days (when 330 L a day is supplied, about 1 ton is produced in 3 days) while being supplied with *Amphidinium carterae* of 7,000 cells/ml as preys. When one *Oxyrrhis marina* feeds on 20 to 25 *Amphidinium carterae* a day and is divided 5 times for 3 days, *Oxyrrhis marina* of 30,000 cells/ml was produced to 2 tons in 3 days. They were harvested using a continuous centrifugal separator, and about 700 g (wet weight) was obtained. The result was dried using a freeze-dryer to remove water, and about 70 to about 80 g (dry weight) was obtained. Biodiesel was extracted using this dried result.

EXAMPLE 4

Production of Bioenergy

The components in cells were extracted from the dried *Oxyrrhis marina* (dry weight: 50 g) using methanol and chloroform as solvents, only a chloroform layer having fatty acids and their derivatives dissolved therein was putted in an evaporator, and chloroform was evaporated to obtain the fatty acids and their derivatives. The content of the obtained fatty acids and their derivatives was 30 to 55% of the total dry weight.

Methanolic HCl was added to the oil type of fatty acids and their derivatives, followed by transesterification at 80° C. for 2 hours for conversion into biodiesel. It was found through this experiment that the total content of fatty acids and their derivatives obtained from 50 g (dry weight) of *Oxyrrhis marina* was 15 to 27 g, and a conversion amount into biodiesel was 4.5 to 16.2 ml, that is, 30 to 60% of the total content of fatty acids and their derivatives, and accordingly, 8 to 15% of *Oxyrrhis marina* was converted into biodiesel.

EXAMPLE 5

Estimated Annual Profit Calculated Based on the Above Examples

When *Amphidinium carterae* of $2 \times 10^5$ cells/ml concentration is cultivated in a 5 ton-scale tank while fixing 0.66 tons of carbon hydroxide a day, and 2.5 tons of a culture solution is supplied to a 32.5 ton-scale tank receiving *Oxyrrhis marina* of 600 cells/ml for 3 days to culture predators, biomasses of about 1.3 kg (dry weight) may be harvested from 35 tons of the culture solution. A maximum of 200 ml of biodiesel may be obtained using this.

In other words, it means that about 2 tons of carbon dioxide may be fixed for 3 days, and the fixed carbon dioxide may be converted into 200 ml of biodiesel. When this is calculated by a year, 250 tons of carbon dioxide will be fixed and 73 L of biodiesel will be obtained.

The estimation is calculated based on the experimental materials, and assuming *Oxyrrhis marina* grows up to a maximum concentration of $6\times10^6$ cells/ml, 35,000 L of biodiesel will be produced a year when a growth density of *Oxyrrhis marina* is maximized.

Also, the use of large-scale commercial systems may result in great economical and environmental benefits.

What is claimed is:

1. A method for producing bioenergy comprising:
   (S1) cultivating aquatic plant and/or algae having a greenhouse gas absorbing activity and resistance to toxic substances, while supplying a waste gas mixture to the aquatic plant and/or algae;
   (S2) cultivating predators having a capability to prey on the aquatic plant and/or algae while supplying the aquatic plant and/or algae to the predators;
   (S3) harvesting the predators; and
   (S4) converting the harvested predators into bioenergy,
   wherein the predator is a host, an egg, or a larva of at least one selected from the group consisting of protest, crustacea, helminthes, benthos, *Oxyrrhis marina, Gyrodinium* spp., *Gymnodinium* spp., *Polykrikos* spp., *Protoperidinium* spp., *Pfiesteria* spp., *Stoeckeria* spp., *Luciella* spp., tintinnids, naked ciliate, and rotifer; and
   wherein the aquatic plant and/or algae is at least one selected from the group consisting of *Amphidinium carterae* and *Heterosigma akashiwo, Chattonella* spp., *Rhodomonas salina, Isochrysis* spp., and *cryptophytes, Skelefonema costatum, Chaetoceros curvisetus, Chaetoceros debilis, Chaetoceros didymus, Chaetoceros socialis, Ditylum brightweffii, Hemiaulus sinensis, Leptocylindrus danicus, Odontella aurita, Thalassiosira nordenskioeldii,* and *Chaetoceros* spp., sea mustard, kelp, laver, green laver, and agar seaweed, and sea grass.

2. The method for producing bioenergy according to claim 1, wherein the predator has a high fatty acid content.

3. The method for producing bioenergy according to claim 2, wherein the predator is *Oxyrrhis marina, Gyrodiniddum* spp., *Stoeckeria algicida, Protoperidinium* spp. or mixtures thereof.

4. The method for producing bioenergy according to claim 3, wherein the predator is *Oxyrrhis marina*.

5. The method for producing bioenergy according to claim 1, wherein the aquatic plant and/or algae is at least one selected from the group consisting of *Rhodomonas salina, Amphidinium carterae, Chaetoceros curvisetus, Chaetoceros debilis, Chaetoceros didymus, Chaetoceros socialis, Ditylum brightwellii, Hemiaulus sinensis, Leptocylindrus danicus, Odontella aurita, Skeletonema costatum,* and *Thalassiosira nordenskioeldii*.

6. The method for producing bioenergy according to claim 5, wherein the aquatic plant and/or algae is *Rhodomonas salina, Amphidinium carterae, Skeletonema costatum,* or mixtures thereof.

7. The method for producing bioenergy according to claim 1, wherein the aquatic plant and/or algae is *Amphidinium carterae*, and the predator is *Oxyrrhis marina*.

8. The method for producing bioenergy according to claim 1, wherein the waste gas mixture is gas emitted from power generators, iron works, factories, engines, boilers (district heating, apartment houses), incineration plants, or ship.

9. The method for producing bioenergy according to claim 1, wherein the toxic substance includes sulfur and/or carbon oxide.

10. The method for producing bioenergy according to claim 1, wherein the greenhouse gas includes carbon dioxide and/or methane.

11. The method for producing bioenergy according to claim 1, wherein the step (S4) includes:
    refrigerating and freeze-drying the harvested predators;
    extracting components in the predators by solvent extraction of the dried predators using methanol, chloroform and distilled water;
    separating a chloroform layer comprising fatty acids and their derivatives, and evaporating chloroform to separate pure fatty acids and their derivatives; and
    transesterifying the separated fatty acids and their derivatives using methanolic HCl.

12. The method for producing bioenergy according to claim 1, further comprising:
    before the step (S1), selecting aquatic plant and/or algae having a greenhouse gas absorbing activity and resistance to toxic substances and predators having a capability to prey on the aquatic plant and/or algae.

13. The method for producing bioenergy according to claim 1, further comprising:
    sterilizing solution remaining after harvesting the predators through the step (S3), and re-providing the sterile solution during the step (S1) for cultivating the aquatic plant and/or algae.

* * * * *